United States Patent
Parker et al.

(10) Patent No.: US 8,175,722 B2
(45) Date of Patent: *May 8, 2012

(54) MAINTAINING LOW IMPEDANCE OF ELECTRODES

(75) Inventors: John Parker, Roseville (AU); Dusan Milojevic, Wheelers Hill (AU)

(73) Assignee: Cochlear Limited, NSW (AU)

( * ) Notice: Subject to any disclaimer, the term of this patent is extended or adjusted under 35 U.S.C. 154(b) by 386 days.

This patent is subject to a terminal disclaimer.

(21) Appl. No.: 12/423,562

(22) Filed: Apr. 14, 2009

(65) Prior Publication Data

US 2009/0204177 A1  Aug. 13, 2009

Related U.S. Application Data

(63) Continuation of application No. 11/159,256, filed on Jun. 23, 2005, now Pat. No. 7,519,435.

(30) Foreign Application Priority Data

Jun. 23, 2004 (AU) .............................. 2004903437

(51) Int. Cl.
*A61N 1/05* (2006.01)
(52) U.S. Cl. ......................................... 607/115; 607/121
(58) Field of Classification Search .............. 607/2, 115, 607/116, 121, 137
See application file for complete search history.

(56) References Cited

U.S. PATENT DOCUMENTS

| | | | |
|---|---|---|---|
| 5,653,742 A | 8/1997 | Parker et al. | |
| 5,674,265 A * | 10/1997 | Deschamps et al. | 607/60 |
| 5,786,439 A | 7/1998 | Van Antwerp et al. | |
| 5,833,714 A | 11/1998 | Loeb | |
| 5,853,424 A | 12/1998 | Rise | |
| 5,861,023 A * | 1/1999 | Vachon | 607/121 |
| 6,116,413 A | 9/2000 | Tabor et al. | |
| 6,304,786 B1 | 10/2001 | Heil, Jr. et al. | |
| 6,304,787 B1 | 10/2001 | Kuzma et al. | |
| 6,354,299 B1 * | 3/2002 | Fischell et al. | 128/899 |
| 6,497,729 B1 * | 12/2002 | Moussy et al. | 623/23.57 |
| 7,218,971 B2 | 5/2007 | Heil, Jr. et al. | |
| 7,519,435 B2 * | 4/2009 | Parker et al. | 607/137 |

* cited by examiner

*Primary Examiner* — Brian T Gedeon
(74) *Attorney, Agent, or Firm* — Kilpatrick, Townsend & Stockton, LLP.

(57) ABSTRACT

An implantable tissue-stimulating device for an implantee comprising: an elongate member, and at least one electrode disposed on the elongate member, wherein at least a portion of the device is coated, prior to implantation in the implantee, with a coating configured to at least partially inhibit adhesion of body tissue to the device following implantation, and wherein the coating is removable, after implantation, by an electrochemical cleaning process during which potential of one or more of the at least one electrode is increased and then decreased.

24 Claims, 5 Drawing Sheets

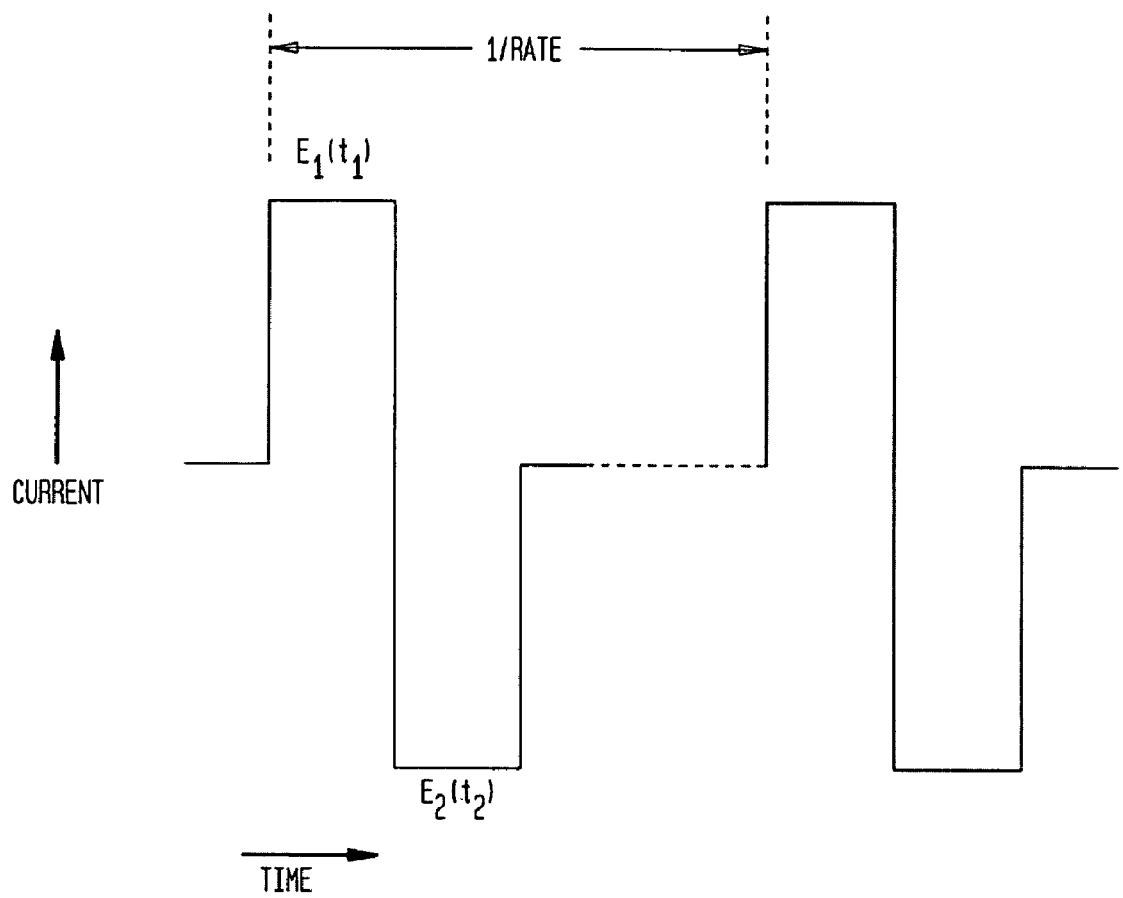

MAINTAINING LOW IMPEDANCE OF ELECTRODES

CROSS-REFERENCE TO RELATED APPLICATIONS

This application is a continuation application of U.S. patent application Ser. No. 11/159,256 entitled "Methods for Maintaining Low Impedance of Electrodes" and filed Jun. 23, 2005, currently pending, which claims the priority of Australian Provisional Application No. 2004903437, entitled, "Methods for Maintaining Low Impedance of Electrodes," filed Jun. 23, 2004. The entire disclosure and contents of the above applications are hereby incorporated by reference herein.

BACKGROUND

1. Field of the Invention

The present application relates generally to electrodes in implantable tissue-stimulating devices, and more particularly, to maintaining low impedance of electrodes in implantable tissue-stimulating devices.

2. Related Art

Studies have demonstrated that a build up of tissue growth occurs on and/or around the electrodes of a hearing implant electrode array following implantation. This occurs as a consequence of an interaction between the body and the implant, perhaps as a result of an injury to the body caused by the implantation or simply due to deposition of organic molecules from the perilymph within the cochlea. The deposition of material on the electrodes following implantation will in most instances increase the impedance of the electrodes and so influence the power consumption and efficiency of the hearing implant.

SUMMARY

In one aspect of the present invention, an implantable tissue-stimulating device is provided. The device comprises an elongate member, and at least one electrode disposed on the elongate member, wherein at least a portion of the device is coated, prior to implantation in the implantee, with a coating configured to at least partially inhibit adhesion of body tissue to the device following implantation, and wherein the coating is removable, after implantation, by an electrochemical cleaning process during which potential of one or more of the at least one electrode is increased and then decreased.

In another aspect of the present invention, method of modifying the surface of at least a portion of an implantable tissue stimulating device is provided. The method comprises providing the tissue stimulating device having at least one electrode having a coating disposed thereon configured to at least partially inhibit adhesion of body tissue to the device following implantation, and removing the coating by an electrochemical cleaning process by increasing and then decreasing the potential of the at least one electrode.

In a yet further embodiment of the present invention, an implantable apparatus for delivering electrical stimulation to an implantee is provided. The apparatus comprises: an elongate member, having at least one electrode supported thereon configured to receive informative stimuli and an inhibitory stimulation signal and to deliver the informative stimuli and the inhibitory stimulation signal to the implantee, wherein the inhibitory stimulation signal is configured to inhibit adherence of body tissue on the implantable device, and a stimulator device configured to generate the informative stimuli and the inhibitory stimulation signal, wherein the inhibitory stimulation signal is configured to have a magnitude below the auditory perception threshold of the implantee, wherein the inhibitory signal comprises at least one pair of anodic and cathodic phases and is configured to at least partially inhibit adhesion of body tissue to the elongate member in a region proximal the at least one electrode, and further wherein the stimulator device is configured to generate the inhibitory stimulation signal after implantation of the apparatus.

BRIEF DESCRIPTION OF THE DRAWINGS

Illustrative embodiments of the present invention are described herein with reference to the accompanying drawings, in which:

FIG. 3 is a graph of an electric current waveform for inhibiting molecular deposition on an electrode array, according to one embodiment of the present invention;

DETAILED DESCRIPTION

The power consumption and efficiency of a tissue-stimulating device, such as a cochlear implant, depends on the impedance of the electrodes positioned on the intracochlear electrode array. Factors that are thought to increase the impedance of the electrodes include adsorption of organic molecules onto and around the electrodes and subsequent growth of fibrous tissue on and around the electrodes or on the surrounding elongate member supporting them.

Figure 1:
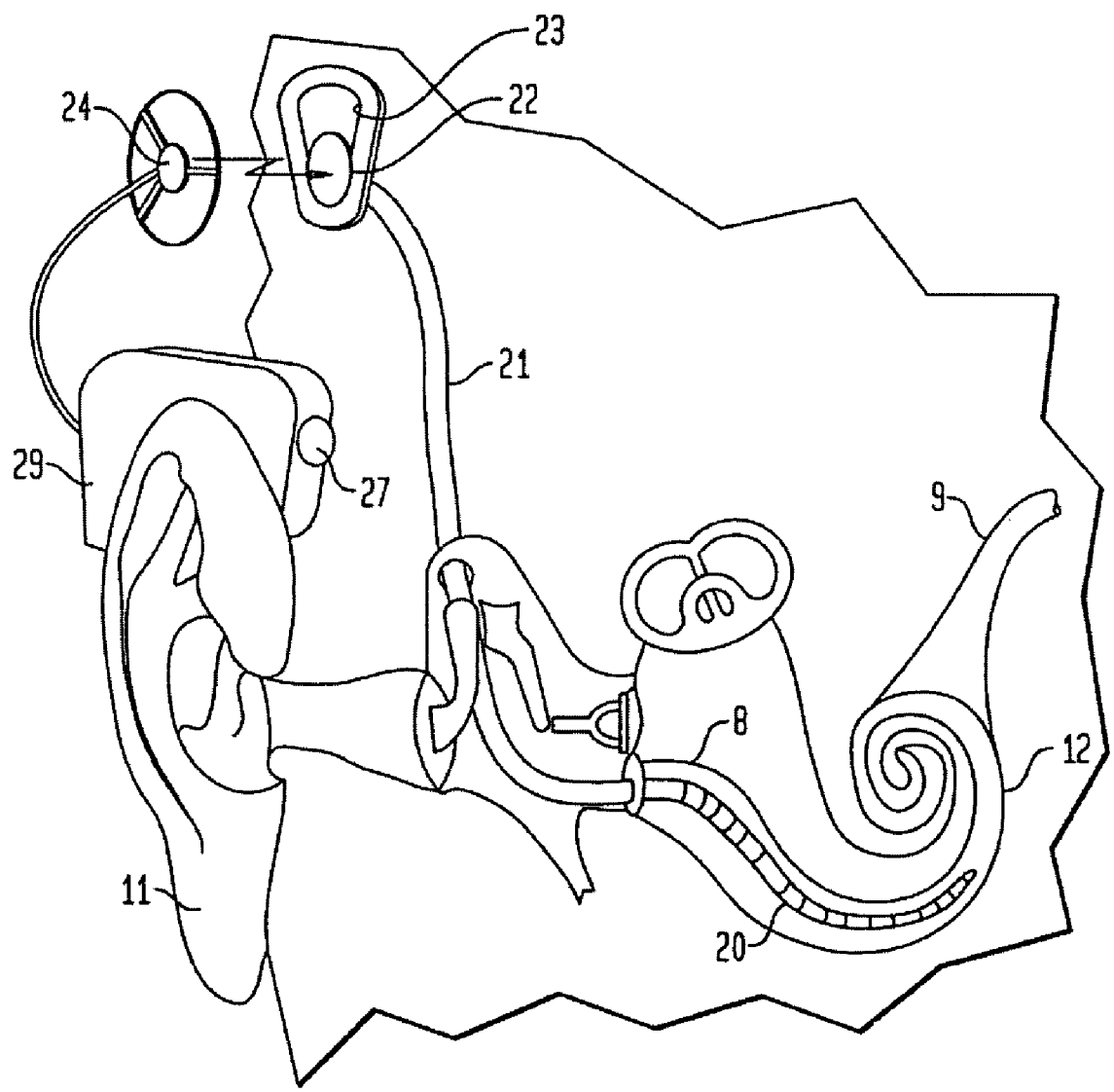
FIG. 1 is a perspective view of an exemplary medical device, namely a hearing implant, in which embodiments of the present invention may be advantageously implemented.
Figure 2:
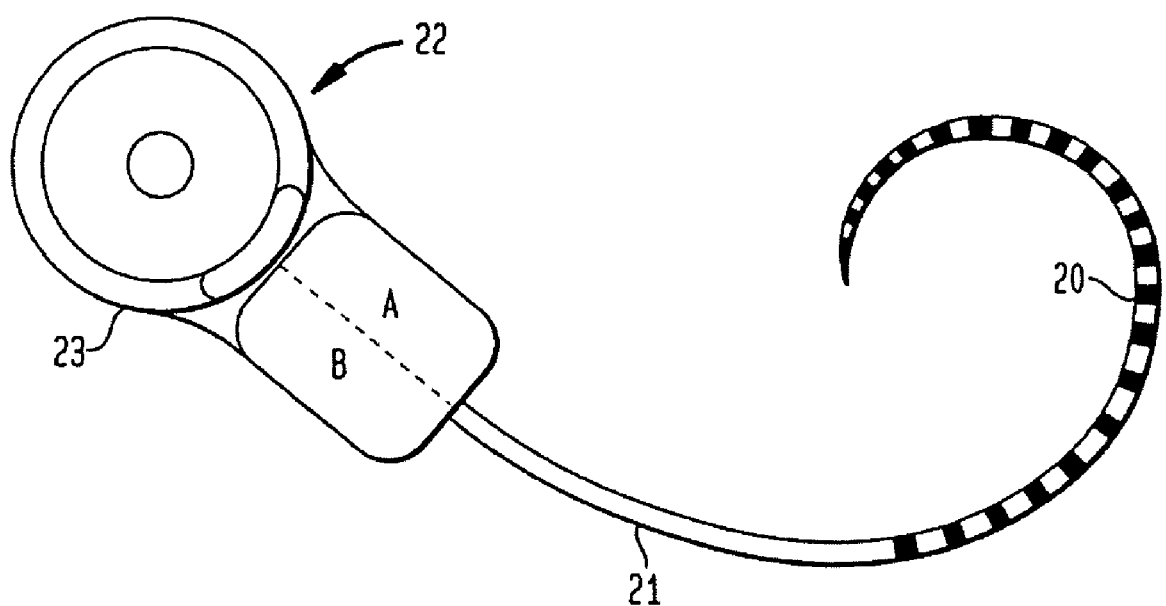
FIG. 2 is a top view of an implantable component, according to one embodiment of the present invention.

An exemplary hearing implant in which embodiments of the present invention may be advantageously implemented is depicted in FIGS. 1 and 2. While for the purposes of this description, a cochlear implant is depicted it will be appreciated that other devices for stimulating other locations of an implantee can be envisaged and are encompassed within the present application.

The hearing implant of FIG. 1 comprises two main components, namely an external component including an external housing containing a speech processor 29, and an internal component including an implanted receiver and stimulator unit 22. The external component includes a microphone 27. The speech processor 29 is, in this illustration, constructed and arranged so that it can be mounted on and fit behind the outer ear 11. It will be understood that in an alternative embodiment of the present invention, the housing for the speech processor 29 and/or the microphone 27 may be worn on the body. Attached to the speech processor 29 is an external antenna coil 24 which transmits electrical signals to the implanted unit 22 via a frequency modulated (FM) radio frequency (RF) link.

The implanted component includes a receiver antenna coil 23 for receiving power and data from the transmitter coil 24. A cable 21 extends from the implanted receiver and stimulator unit 22 to the cochlea 12 and terminates in an electrode array 20. The data signals thus received are decoded and applied as current pulses by the array 20 thereby stimulating the auditory nerve 9.

It will be appreciated that whilst the embodiment illustrated in FIG. 1 depicts a system having internal and external components, in other embodiments of the present invention the system is equally applicable to a fully implantable system whereby the components are contained in one or more housings implanted within the recipient.

In addition to the array 20 being capable of delivering auditory stimuli to the modiolus 8, the hearing implant is adapted to deliver stimulation that at least partially inhibits organic molecule adhesion to the electrodes of the array. As depicted in FIG. 2, the housing of the unit 22 can comprise a portion A that contains what would be regarded as the traditional circuitry of the implant so that the implant can function as a traditional hearing implant. It also comprises a portion B that houses appropriate circuitry to allow the electrode array 20 to deliver the stimulation that inhibits organic molecular adhesion as defined herein.

In one exemplary application of the present invention, the inhibitory stimulation has a magnitude less than the auditory perception threshold of the implantee and as such does not cause the implantee to perceive a sound which is in contrast to the case when the implant delivers an auditory stimuli.

The inhibitory stimulation may be delivered after surgical implantation of the implant and prior to activation of the implant to deliver auditory informative stimuli to the implantee. Once auditory informative stimuli is delivered, the implant may, in one embodiment, operate so as to never again deliver inhibitory stimulation, with the auditory stimuli themselves acting to inhibit tissue growth. Alternatively, the apparatus may be operable so as to deliver such inhibitory stimulation at times when the implant is not delivering auditory informative stimuli. For example, the implant might deliver inhibitory stimulation to the cochlea overnight when the implantee does not wish to receive auditory informative stimuli or when the apparatus is inactive for other reasons.

It is anticipated that it would be desirable to deliver the inhibitory stimulation as soon as possible after implantation of the array 20. In one embodiment, the array 20 is operable so as to be delivering inhibitory stimulation during implantation of the array 20. The length of time that the implantee receives the inhibitory stimulation will be dependent on factors such as how quickly it is decided to activate the implant for delivery of auditory informative stimuli. In one embodiment of the present invention, the inhibitory stimulation is delivered for up to 12 weeks following implantation of the array 20 at which point the implant is typically activated or "switched on". This is due to the fact that the immune responses that cause fibrous tissue growth are triggered by any damage to the cochlea structures which may be caused during insertion of the array 20. These immune responses are typically complete after 12 weeks and as such fibrous tissue growth after this time will be minimal.

In a further embodiment, for instances where individuals have not received inhibitory stimulation immediately following implantation, an inhibitory stimulation of a different type may be applied. This different type of inhibitory stimulation is in the form of a concentrated stimulation for a specific period of time at an intensity and rate configured to partially or wholly remove fibrous tissue from the electrodes. Following this concentrated stimulation, normal inhibitory stimulation may be employed to prevent any further growth.

As depicted by FIG. 3, the inhibitory stimulation can comprise an anodic pulse. In one embodiment, the anodic pulse is in the form of a large positive potential excursion such that it desorbs organic molecules from the one or more electrodes. This would also result in oxidization of the electrode. In this embodiment, the anodic pulse is followed by a cathodic pulse. Again, in this embodiment, the cathodic pulse is in the form of a large negative potential such that it dissolves the oxide back to its metal state. The stimulation thus has an oscillating waveform. It will be appreciated that the waveform can be more complex and/or asymmetric in other embodiments of the present invention. For example, in another embodiment, the waveform is square, as depicted in FIG. 3 or, in another embodiment, sinusoidal where the anodic and cathodic pulse may be symmetrical or asymmetrical but in any case charge balanced. In further embodiments of the present invention, the waveform also has phases of much wider duration than that shown (with less current to maintain the sub-threshold level) and is even superimposed with a normal auditory stimulus waveform for delivering sound signals.

It will also be appreciated that the rate of application of inhibitory stimulus pulses is very low (e.g. one per minute) in certain embodiments of the present invention in order to conserve the power efficiency of the device. In this regard, the specific rate of application will be optimized to be as low as possible in order to retain the electrodes clear of fibrous tissue.

In certain embodiments, the implantable unit 22 is modified so as to house a power source, such as one or more rechargeable batteries. This power source may have sufficient power to allow the implant to deliver inhibitory stimulation even when the external component is not being used and the implantee is unable to receive auditory informative stimuli. This is advantageous as it allows the system to deliver the inhibitory stimulation at any time such as when the implantee is asleep.

In certain embodiments, the electronics housed in the implantable unit is provided with a clock, controlling the overall operation of the implant. This clock controls the timing as to when the inhibitory stimulation is delivered. In some embodiments, this clock is programmable to operate in "real time" such that the recipient receives the inhibitory stimulation at times when the recipient is asleep or not receiving auditory informative stimuli. Such a clock would ideally take into consideration time changes and personal settings, such as shift work etc, and would therefore be controllable through an external device, such as the conventional external speech processor 29. Further, the electronics may also be programmed to initiate the inhibitory stimulus whenever auditory stimulus ceases.

In certain embodiments of the present invention, the electrodes and/or the elongate member of the array 20 are coated with a coating that at least partially inhibits adhesion of organic molecules to said device following implantation. In certain embodiments, the coating is present on an array 20 of a device that delivers inhibitory stimulation. In other embodiments of the present invention, the coating is used on a hearing implant array or the array of other tissue-stimulating devices that are not adapted to deliver inhibitory stimulation.

In some embodiments, the inhibiting coating is a hydrophilic polymer or a derivative thereof. Examples of suitable polymers include water-soluble linear or branched polymers including but not limited to polyethylene glycol (PEG) and polypropylene oxide (PPO) and similar linear and branched polymers and derivatives thereof.

In these embodiments, the elongate member is covered with a continuous coating. In other embodiments, some or all of the elongate member is covered by a coating that has a surface pattern. The surface pattern influences the tissue growth, by inhibiting such growth, encouraging such growth and/or influencing the direction of any growth.

Figure 4A:
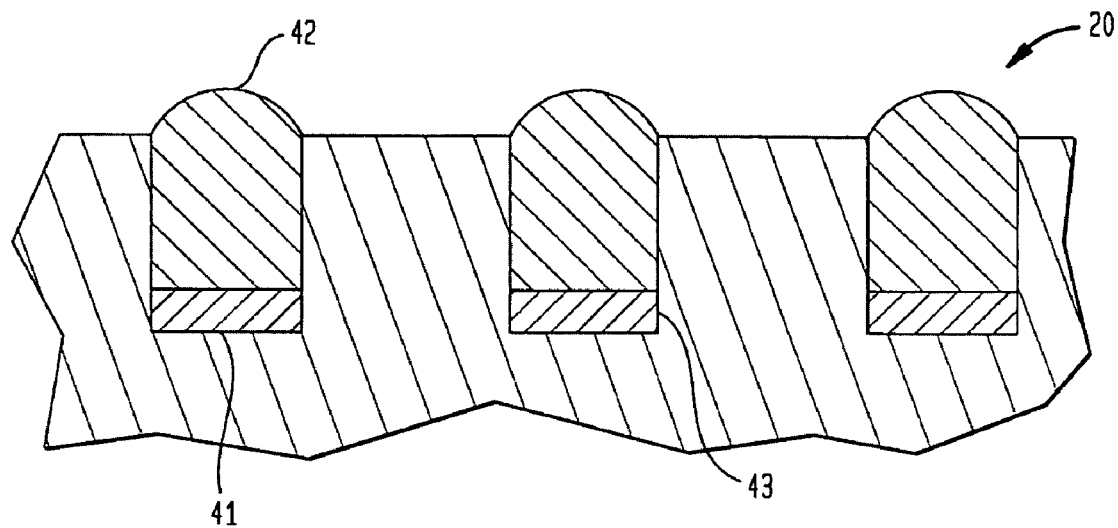
FIGS. 4a and 4b are cross-sectional views of electrodes of an array having a coating that inhibits molecular deposition, according to one embodiment of the present invention.
Figure 4B:
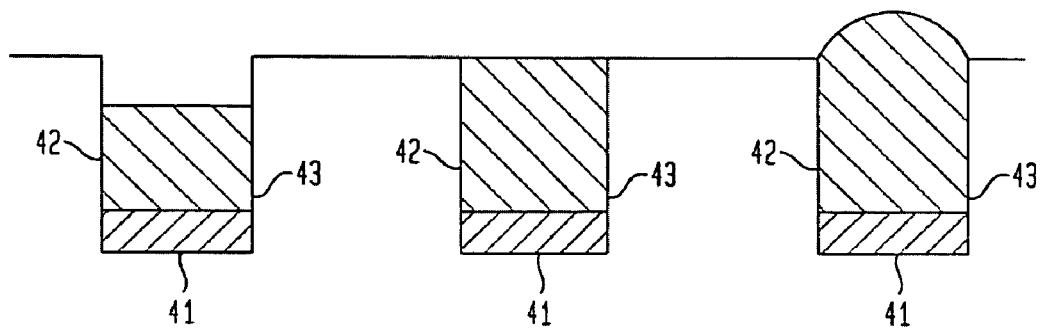

In the embodiments depicted in FIGS. 4a and 4b, the electrodes 41 have a layer of biocompatible and water soluble polyethylene glycol (PEG) 42, or a PEG derivative, deposited thereon. PEG has the following structure:

$$HO\text{---}(\text{---}CH_2CH_2O\text{---})_n\text{---}H.$$

Derivatives of the hydrophilic polymer may be formed by chemical modification and/or conjugation reactions. For example, derivatives of PEG and PPO include but are not limited to thiols, silanes, ethers, esters, amides, amines, acids and aldehydes. The PEG can include functional groups that enable functional bonding between the coating and the material of the electrodes 41. In those embodiments in which the electrode is formed from gold or platinum or has a surface formed from such a material, the PEG structure can include, for example, thiol or silane functional groups.

In some embodiments, the PEG coating has a melting point greater than room temperature and indeed has a melting point higher than 50° C. As shown in FIG. 4a, the electrode array 20 is kept at room temperature, a drop of melted PEG can be deposited on the electrodes 41 that are each positioned in a respective recess 43. Once deposited, the PEG will cool and solidify promptly leaving a temporary coating on the electrodes 41.

As depicted in FIG. 4b, in some embodiments of the present invention, the quantity of coating applied in each electrode recess is such that the outer surface of the solidified coating 42 is below the top of the recess, at or about the top of the recess, or is proud of the top of the recess 43.

When coating 42 is soluble, the coating is expected to have a limited lifespan following implantation. In this regard, the lifespan in certain embodiments of the present invention can be less than 3 months, more preferably less than 2 months. In other embodiments, it could also be arranged that the coating is designed to last until about the expected date when the implant is to be activated. In this regard, the implant is activated within 12 weeks following implantation in certain embodiments of the present invention.

In certain embodiments, the coating 42 is removable by an electrochemical cleaning process, such as the pulsing sequence depicted in FIG. 3. As described, this comprises increasing the potential of the electrodes 41 to a level where oxidation of the electrode material occurs and reducing the potential to a level where the oxide is reduced back to a metallic state. In such embodiments, during the oxidation step, any remnants of the coating are stripped off the electrode surface leaving it in an oxidised state that is subsequently reduced back to the metal. It is to be appreciated that, in other embodiments, a cleaning action may be achieved without fully oxidizing and reducing the surface of the electrodes.

In other embodiments of the present invention, the coating is in the form of a gel or gel-like mass. In such embodiments, the gel or gel-like mass is formed by dissolving the coating material, prior to deposition, in a suitable solvent, such as water, at, for example, an elevated temperature and then caused to solidify by allowing the material to reduce in temperature to a temperature below the melting point of the material. The solvent can contain a solute, such as a salt, for example, sodium chloride. This results in the coating having at least a degree of electrical conductivity.

Figure 5A:
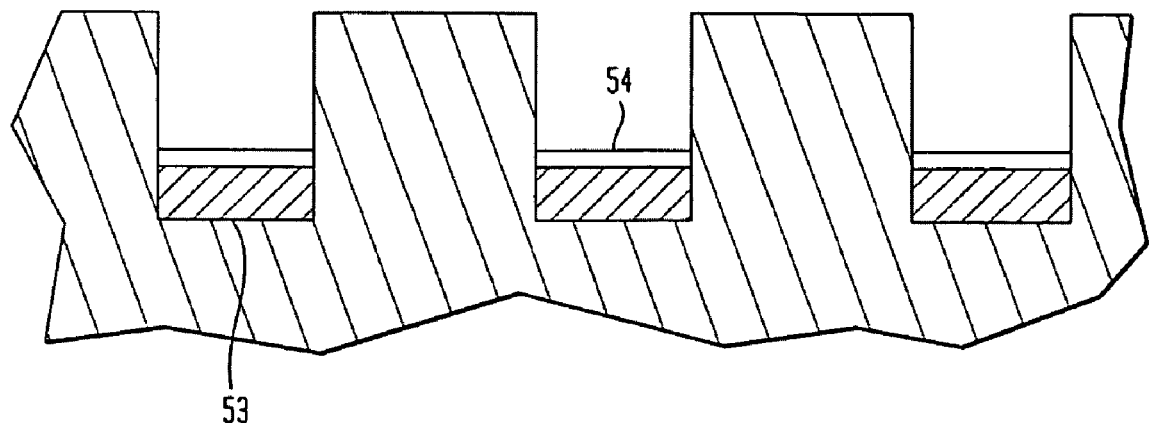
FIGS. 5a and 5b are cross-sectional views of electrodes and an array, respectively, having a monolayer coating, according to one embodiment of the present invention.
Figure 5B:
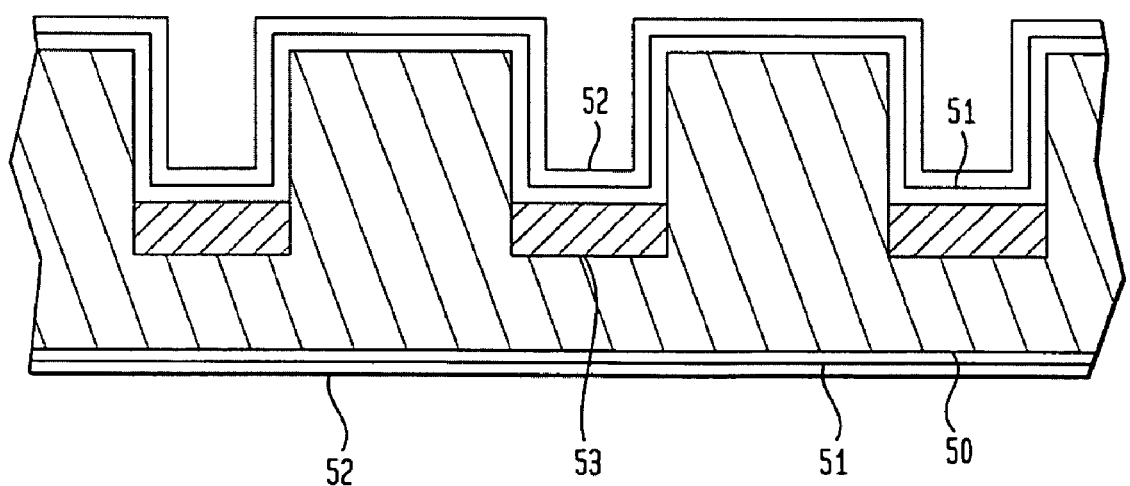

In certain embodiments of the present invention, each of the electrodes and/or the elongate member of the array has a coating that is semi-permanent or permanent. Such coatings can have a property of at least allowing partial access, more preferably unimpaired access, of ions to the electrode surface, while minimizing protein adsorption at the same surface. Such a coating can comprise a self-assembled monolayer. Such a monolayer 54 is coated only on the electrodes 53 (as depicted in FIG. 5a) in certain embodiments, or can be coated over all of the array 20 (as depicted in FIG. 5b) in other embodiments. For example, in the embodiment illustrated in FIG. 5b, the elongate member of the array is formed of a silicone 50, a layer of a suitable metal 51 is firstly applied to the elongate member. In one exemplary embodiment, this layer 55 can be gold and have a thickness of less than 10 nanometres. Such a layer 51 may be applied using a sputtering or evaporation technique. Due to its thinness, it is anticipated that the layer 51 would overall be electrically conductive and as such would not affect the electrical functionality of the device. A monolayer coating 52 would then be deposited on the layer 51 of suitable metal.

Typically, the elongate member of the array 20 is formed from a suitable biocompatible material. As already described, that material is a silicone in certain embodiments, such as Silastic MDX 4-4210. In other embodiments, the elongate member is formed from a polyurethane.

In certain embodiments, each electrode is formed from a biocompatible material, such as platinum. In one embodiment, the electrode array 20 comprises 22 platinum electrodes spaced along the elongate member.

In other embodiments of the present invention may, the implant system includes one or more capacitively coupled extracochlea electrodes to support monopolar stimulation, as is known in the art.

It will be appreciated by persons skilled in the art that numerous variations and/or modifications may be made to the invention as shown in the specific embodiments without departing from the spirit or scope of the invention as broadly described. The present embodiments are, therefore, to be considered in all respects illustrative and not restrictive.

What is claimed is:

1. A method of modifying the surface of at least a portion of an implantable tissue stimulating device, the method comprising:
   providing the tissue stimulating device having at least one electrode having a coating disposed thereon configured to at least partially inhibit adhesion of body tissue to said device following implantation; and
   removing the coating by an electrochemical cleaning process by increasing and then decreasing the potential of the at least one electrode.

2. The method of claim 1, wherein the coating is polyethylene glycol (PEG).

3. The method of claim 1, wherein the coating has functional groups that enable functional bonding between the coating and said portion of the device.

4. The method of claim 3, wherein the functional groups enable functional bonding between the coating and an electrically active surface of said at least one electrode.

5. The method of claim 4, wherein the electrically active electrode surface is gold or platinum.

6. The method of claim 1, wherein said one or more of said at least one electrode is coated with said coating.

7. The method of claim 1, wherein the coating is applied to each of said at least one electrode in a liquid form which is configured to become a solid subsequent to application.

8. The method of claim 1, wherein the coating is bioresorbable following implantation.

9. The method of claim 1, wherein said coating comprises at least one solute.

10. The method of claim 1, wherein the coating is configured to be a self-assembled monolayer.

11. The method of claim 1, wherein the tissue-stimulating device is a cochlear implant.

12. The method of claim 1, wherein the coating is a water soluble coating.

13. The method of claim 12, wherein said water soluble coating is configured to have a life-span of approximately three months or less.

14. The method of claim 12, wherein said water soluble coating is configured to have a life-span of approximately two months or less.

15. The method of claim 1, wherein the coating is configured as a surface pattern.

16. The method of claim 1, wherein said coating is disposed on only the electrode.

17. An implantable apparatus for delivering electrical stimulation to an implantee, comprising:
    an elongate member, having at least one electrode supported thereon configured to receive informative stimuli and an inhibitory stimulation signal and to deliver said informative stimuli and the inhibitory stimulation signal to the implantee, wherein said inhibitory stimulation signal is configured to inhibit adherence of body tissue on said implantable device; and
    a stimulator device configured to generate said informative stimuli and said inhibitory stimulation signal, and to configure said inhibitory stimulation signal to have a magnitude below the auditory perception threshold of the implantee, wherein said inhibitory signal comprises at least one pair of anodic and cathodic phases and is configured to at least partially inhibit adhesion of body tissue to said elongate member in a region proximal the at least one electrode, and further wherein said stimulator device is configured to generate said inhibitory stimulation signal after implantation of said apparatus at times including a time when said implantable apparatus is not delivering auditory informative stimuli to said implantee.

18. The implantable apparatus of claim 17, wherein said stimulator device is configured to generate said inhibitory stimulation signal at a rate of approximately equal to or less than one per minute.

19. The implantable apparatus of claim 17, wherein said stimulator device is controllably coupled to a clock, said stimulator device being configured to generate said inhibitory stimulation signal based on said clock.

20. The implantable apparatus of claim 19, wherein said stimulator device is configured to receive programming instructions from at least one of the recipient or a clinician for generating said inhibitory stimulation based on said clock.

21. A method of modifying the surface of at least a portion of an implantable tissue stimulating device including an elongate member having a plurality of electrodes supported thereon configured to receive informative stimuli and an inhibitory stimulation signal and to deliver said informative stimuli and the inhibitory stimulation signal to an implantee, the method comprising:
    generating an inhibitory stimulation signal configured to have a magnitude below an auditory perception threshold of the implantee and to have at least one pair of anodic and cathodic phases so as to at least partially inhibit adhesion of body tissue to said elongate member in a region proximal the at least one electrode; and
    applying said inhibitory stimulation signal after implantation of said apparatus at times including a time when said implantable apparatus is not delivering auditory informative stimuli to said implantee.

22. The method of claim 21, wherein said step of generating further includes:
    setting said rate to be approximately equal to or less than one per minute.

23. The method of claim 21, wherein said stimulator device is controllably coupled to a clock, said stimulator device being configured to generate said inhibitory stimulation signal based on said clock.

24. The implantable apparatus of claim 21, wherein said stimulator device is configured to receive programming instructions from at least one of the recipient or a clinician for generating said inhibitory stimulation based on said clock.

* * * * *